United States Patent
Grigsby

(10) Patent No.: US 10,322,298 B2
(45) Date of Patent: Jun. 18, 2019

(54) DEVICES AND METHODS FOR TREATMENT OF CANCERS

(71) Applicant: Washington University, St. Louis, MO (US)

(72) Inventor: Perry W. Grigsby, Glendale, MO (US)

(73) Assignee: Washington University, St. Louis, MO (US)

( * ) Notice: Subject to any disclaimer, the term of this patent is extended or adjusted under 35 U.S.C. 154(b) by 542 days.

(21) Appl. No.: 14/254,054

(22) Filed: Apr. 16, 2014

(65) Prior Publication Data

US 2014/0309478 A1    Oct. 16, 2014

Related U.S. Application Data

(60) Provisional application No. 61/812,404, filed on Apr. 16, 2013.

(51) Int. Cl.
*A61N 5/00* (2006.01)
*A61N 5/10* (2006.01)

(52) U.S. Cl.
CPC ......... *A61N 5/1016* (2013.01); *A61N 5/1007* (2013.01); *A61N 2005/1012* (2013.01); *A61N 2005/1018* (2013.01)

(58) Field of Classification Search
CPC .... A61N 2005/1012; A61N 2005/1018; A61N 5/1016; A61N 5/1014
See application file for complete search history.

(56) References Cited

U.S. PATENT DOCUMENTS

| 2007/0020311 A1* | 1/2007 | Browning | A61F 6/142 424/426 |
| 2009/0234177 A1* | 9/2009 | Lebovic | A61N 5/1016 600/6 |
| 2011/0224478 A1* | 9/2011 | Hannoun-Levi | A61N 5/1016 600/6 |

* cited by examiner

*Primary Examiner* — John P Lacyk
(74) *Attorney, Agent, or Firm* — Armstrong Teasdale LLP

(57) ABSTRACT

Devices and methods for brachytherapy treatment are disclosed. One aspect is a poly(methyl methacrylate) apparatus for brachytherapy treatment at the vaginal apex. Another aspect is a poly(methyl methacrylate) apparatus for brachytherapy treatment in the distal two-thirds of the vagina. Another aspect is a poly(methyl methacrylate) apparatus for brachytherapy treatment of cancers that are offset from the vaginal apex. Other aspects include methods for guiding needles for treatment of cancers at the vaginal apex, in the distal two-thirds of the vagina, and that are offset from the vaginal apex.

12 Claims, 7 Drawing Sheets

DEVICES AND METHODS FOR TREATMENT OF CANCERS

CROSS-REFERENCE TO RELATED APPLICATION

This application claims priority to U.S. patent application Ser. No. 61/812,404, filed on Apr. 16, 2013, the disclosure of which is hereby expressly incorporated by reference in its entirety.

BACKGROUND

The present disclosure relates generally to devices for treatment of cancers. More particularly, the present disclosure relates to devices for brachytherapy treatment of cancers in the vaginal, vulvar, anal and urethral regions.

Cancers in the vaginal, vulvar, anal and urethral regions, which include recurrent endometrial and cervical cancers, usually spread into the abdominal wall and are difficult to reach. Many physicians thus use a laparotomy to reach the tumor site. In this procedure, a large incision is made through the abdominal wall to gain access into the abdominal cavity. Needles that are to deliver the radiotherapy are then placed through the tumor via the abdominal side and the vaginal side of the tumor. This method requires inpatient status and is invasive.

Interstitial brachytherapy allows for radioactive implants to be placed directly into the tumor. This form of brachytherapy is usually reserved for patients that have extensive pelvic and/or vaginal disease in an attempt to improve local control or those patients with anatomy that does not allow for intracavitary brachytherapy with standard applicators (for example, patients having had a hysterectomy, narrow vagina, etc).

Devices such as the Syed-Neblett template are commonly used for interstitial brachytherapy treatment of primary vaginal, vulvar, cervix and urethral cancers. The Syed-Neblett template consists of two superimposed heavy plastic plates held together by metallic screws. The Syed-Neblett template is sutured in place on the perineum. Pre-drilled holes in the template accept the needles that are guided to and ultimately placed within the tumor. A large hole in the middle of the template allows for insertion of radiation sources. Because of the heavy plastic and metallic screws, the Syed-Neblett template may elicit pain in the patient that requires epidural treatment for pain management, and thus, inpatient status.

While the devices are suitable for placing radioactive implants directly into the tumor, they can require surgery and require inpatient status. Accordingly, there exists a need to develop devices and non-invasive methods for delivering radiotherapy in a manner that allows patients to be treated on an outpatient basis and without requiring surgery.

BRIEF DESCRIPTION

The present disclosure is generally directed to devices for treatment of cancers. More particularly, the present disclosure relates to devices for brachytherapy treatment of cancers in the vaginal, vulvar, anal and urethral regions of a patient.

In one aspect, the present disclosure is directed to a poly(methyl methacrylate) apparatus for brachytherapy treatment at the vaginal apex. The poly(methyl methacrylate) apparatus comprises: a) a vaginal cylinder comprising a plurality of apertures arranged in a square pattern for receiving a plurality of needles and a central aperture for receiving a central rod; and b) a distal template comprising a plurality of apertures arranged in a square pattern for receiving a plurality of needles and a central aperture for receiving the central rod; wherein the plurality of apertures in the vaginal cylinder and the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template. The central rod may further include an aperture for receiving a needle or a catheter. The square pattern of the apertures of the apparatus allows for a dose cloud at the apex of the vagina.

In another aspect, the present disclosure is directed to a poly(methyl methacrylate) apparatus for brachytherapy treatment in the distal two-thirds of the vagina. The poly(methyl methacrylate) apparatus comprises a) a vaginal cylinder comprising a plurality of apertures arranged in a circular pattern for receiving a plurality of needles and a central aperture for receiving a central rod; and b) a distal template comprising a plurality of apertures arranged in a circular pattern for receiving a plurality of needles and a central aperture for receiving the central rod; wherein the plurality of apertures in the vaginal cylinder and an inner ring of the plurality of needles of the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template. The central rod may further include an aperture for receiving a needle or a catheter. The circular pattern of the apertures of the apparatus allows for a crescent-shaped dose distribution.

In another aspect, the present disclosure is directed to an apparatus for brachytherapy treatment of cancers that are offset from the vaginal apex. The apparatus comprises a) a proximal poly(methyl methacrylate) template comprising a plurality of apertures for receiving a plurality of needles; and b) a distal poly(methyl methacrylate) template comprising a plurality of apertures for receiving a plurality of needles.

In another aspect, the present disclosure is directed to a method for guiding a plurality of needles to a tumor for brachytherapy treatment at the vaginal apex, the method comprising: a) positioning adjacent to the tumor a proximal end of a vaginal cylinder of a poly(methyl methacrylate) apparatus, wherein the poly(methyl methacrylate) apparatus comprises: i) a vaginal cylinder comprising a plurality of apertures arranged in a square pattern for receiving a plurality of needles and a central aperture for receiving a central rod; and ii) a distal template comprising a plurality of apertures arranged in a square pattern for receiving a plurality of needles and a central aperture for receiving the central rod; wherein the plurality of apertures in the vaginal cylinder and the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template; b) fastening the apparatus in place; and c) inserting the plurality of needles through the plurality of apertures of the apparatus such that the plurality of needles extend through the plurality of apertures of the vaginal cylinder to a position adjacent to the tumor.

In another aspect, the present disclosure is directed to a method for guiding a plurality of needles to a tumor for brachytherapy treatment in the distal two-thirds of the vagina, the method comprising: a) positioning adjacent to the tumor a proximal end of a vaginal cylinder of a poly (methyl methacrylate) apparatus, wherein the apparatus comprises: i) a vaginal cylinder comprising a plurality of apertures arranged in a circular pattern for receiving a plurality of needles and a central aperture for receiving a central rod; and ii) a distal template comprising a plurality of apertures arranged in a circular pattern for receiving a plurality of needles and a central aperture for receiving the central rod; wherein the plurality of apertures in the vaginal cylinder and an inner ring of the plurality of needles of the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template; b) fastening the apparatus in place; and c) inserting the plurality of needles through the plurality of apertures of the apparatus such that the plurality of needles extend through the channels of the vaginal cylinder to a position adjacent to the tumor; and d) inserting a second plurality of needles through the plurality of apertures of the distal template wherein the second plurality of needles are positioned outside the vaginal cylinder.

In another aspect, the present disclosure is directed to a method for guiding a plurality of needles for treatment of cancers that are offset from the vaginal apex, the method comprising: a) positioning a proximal poly(methyl methacrylate) template of a poly(methyl methacrylate) apparatus adjacent the tumor that is offset from the vaginal apex using a handle; b) fastening the proximal poly(methyl methacrylate) template in place; and c) inserting a plurality of needles through the plurality of apertures of the proximal poly (methyl methacrylate) template such that the plurality of needles extend through the apertures of the proximal poly (methyl methacrylate) template to a position adjacent to the tumor; d) inserting the plurality of needles through the apertures of the distal poly(methyl methacrylate) template; and e) fastening the distal poly(methyl methacrylate) template in place.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
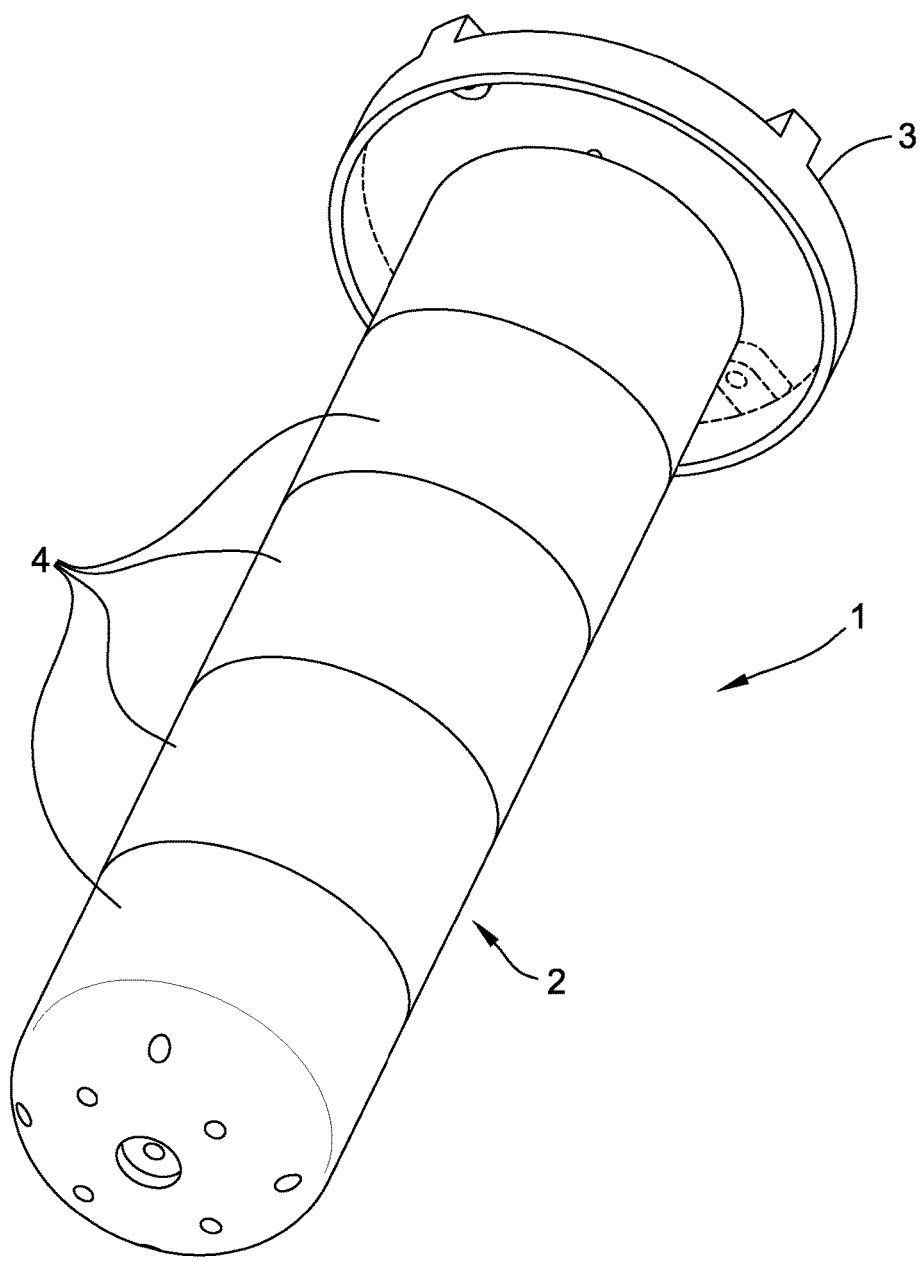
FIG. 1 is a photograph showing an apparatus of the present disclosure having an adjustable length embodiment of a vaginal cylinder and distal template.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

Apparatus for Brachytherapy Treatment of Cancers at the Top of the Vaginal Apex

In accordance with the present disclosure, one aspect of the poly(methyl methacrylate) apparatus includes a vaginal cylinder and a distal template that is used for interstitial implantation of HDR brachytherapy needles into cancer tumors at the true top of the vaginal apex. FIG. 1 is a photograph of one embodiment of the apparatus 1. The apparatus 1 includes a vaginal cylinder 2 and a distal template 3. As used herein, "distal" refers to a region or location furthest from a tumor. Once in position, the distal template 3 can then be fastened such as, for example, by suturing or stapling, to the perineum, for example.

In one embodiment, the length of the vaginal cylinder 2 can be a fixed length (i.e., not adjustable to different lengths). In the fixed length embodiment, the vaginal cylinder 2 can be fabricated to any suitable predetermined length. A distal template can then be releasably coupled to the vaginal cylinder 2 of the appropriate length as determined by one skilled in the art such as, for example, a medical professional, to fit the length of the bodily canal (e.g., the vaginal canal and rectum) in which the apparatus is used such that the proximal end of the vaginal cylinder 2 (see, FIG. 2) can be placed at the tumor site and the distal template 3 can be fastened at a site determined by a medical professional.

In another embodiment, the length of the vaginal cylinder 2 can be adjustable. In the adjustable embodiment, the vaginal cylinder 2 is made up of rings 4 that can be added or removed to lengthen or shorten the vaginal cylinder 2 to a desired length as determined by one skilled in the art such as, for example, a medical professional, such that the proximal end of the vaginal cylinder 2 can be placed at the tumor site. FIG. 1 shows an embodiment of an apparatus with an adjustable length vaginal cylinder 2 made up of five (5) rings 4. However, any number of rings can be used to achieve the desired length such that the proximal end of the vaginal cylinder can be placed at the tumor site.

The shape of the vaginal cylinder 2 can be any desired shape. Generally, the vaginal cylinder 2 should have a maximum diameter that permits insertion of the apparatus 1 within the confines of the bodily canal into which the apparatus 1 is used. A cylindrical shape is particularly suitable.

Figure 2:
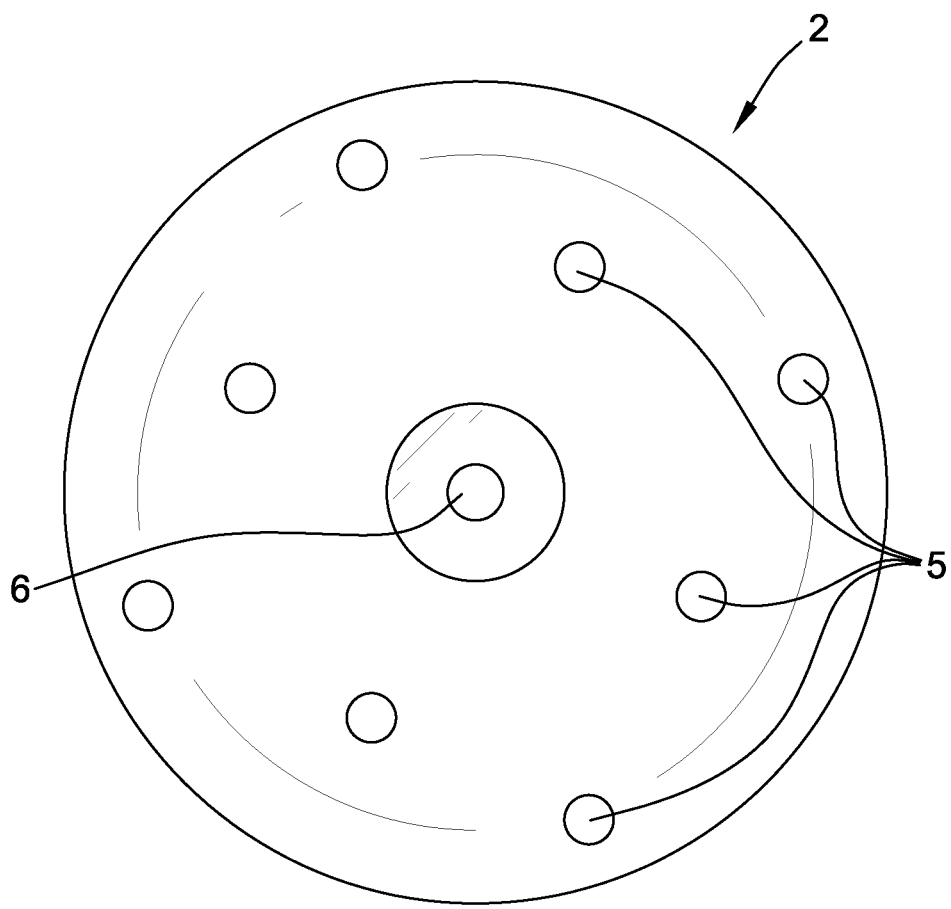
FIG. 2 is an end-on photograph of the vaginal cylinder of an apparatus shown in FIG. 1 showing a plurality of apertures arranged in a square pattern for delivering a dose cloud.

FIG. 2 shows an end-on version of a vaginal cylinder 2 of the apparatus 1. As shown in FIG. 2, the vaginal cylinder 2 includes a plurality of apertures 5 formed in the vaginal cylinder 2 for receiving a plurality of needles (not shown). The apertures 5 are arranged in a square pattern surrounding a central aperture 6 for receiving a central rod (not shown). The central rod connects the vaginal cylinder 2 and the distal template 3 to hold the apparatus 1 together. Additionally, the central rod (not shown) can include an aperture (not shown) that can be used for catheter (not shown) placement or for receiving an additional needle (not shown). FIG. 2 also shows an embodiment of a vaginal cylinder 2 having a tapered circumference (i.e., smooth edge) that advantageously provides comfort during insertion of the apparatus 1 and while in contact with any bodily surfaces.

Figure 3:
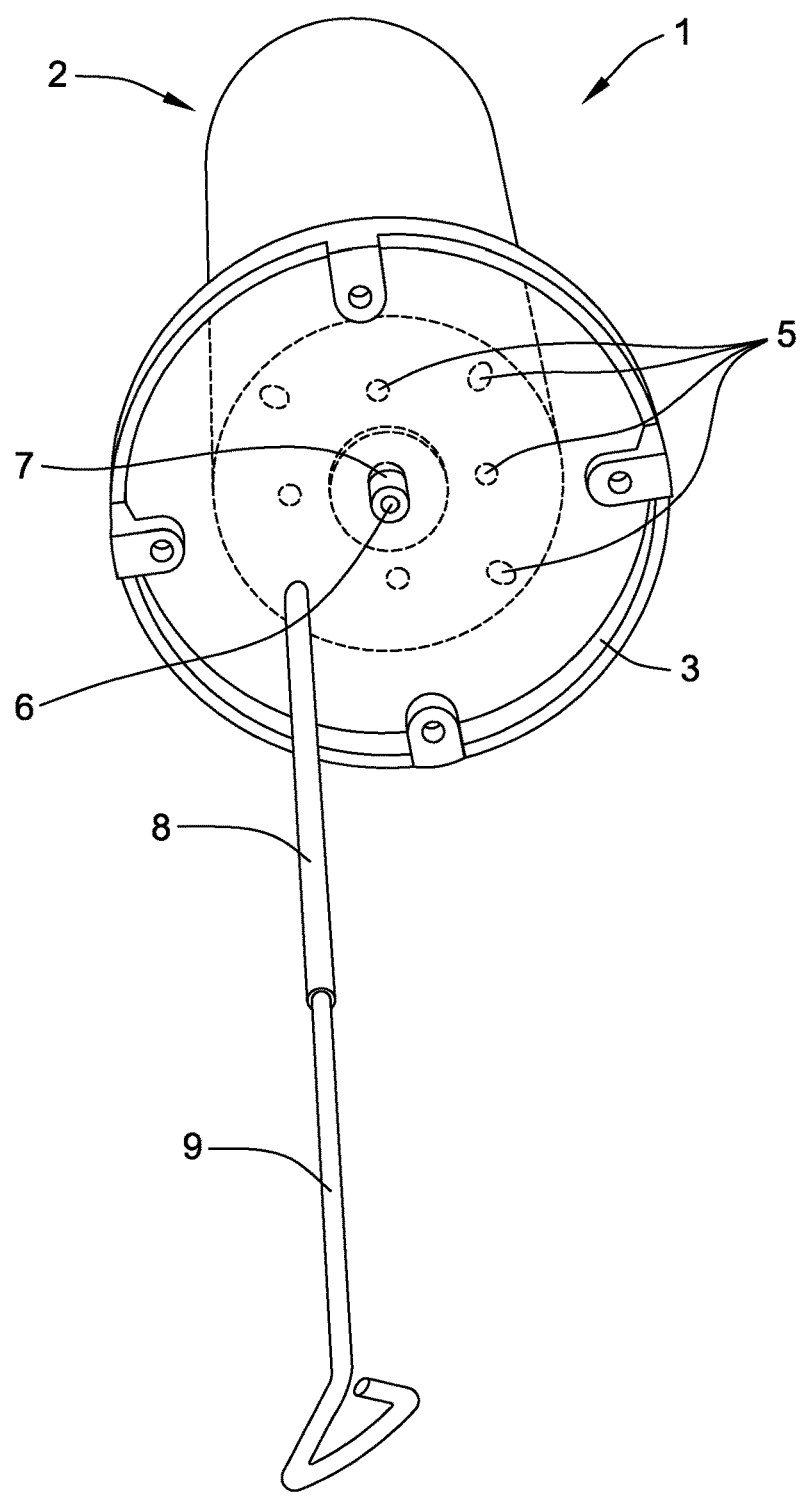
FIG. 3 is an end-on photograph of the distal template of an apparatus of the present disclosure shown in FIG. 1 with a needle and metal rod for placing the needle inserted into an aperture and showing a plurality of apertures arranged in a square pattern that are aligned with the plurality of apertures arranged in a square pattern of the vaginal cylinder to form channels.

As shown in FIG. 3, the distal template 3 includes a plurality of apertures 5 for receiving the plurality of needles. The apertures 5 are arranged in a square pattern surrounding a central aperture 6 for receiving the central rod 7 to hold the apparatus 1 together. Equivalent apertures 5 are formed in the vaginal cylinder 2 of the fixed length embodiment and the rings 5 of the adjustable length vaginal cylinder 2, as well as in the distal template 3. Alignment of the apertures 5 of the vaginal cylinder 2 and the distal template 3 allow for insertion of brachytherapy needles into the apertures 5 of the distal template 3 through the apertures (not shown) of the vaginal cylinder 2 such that the needle tips can be positioned in a tumor or in the region surrounding the tumor for delivery of the treatment. Alignment of the central apertures 6 of the vaginal cylinder 2 and the distal template 3 allow for insertion of the central rod 7 to hold the apparatus together. FIG. 3 shows the central rod 7 containing a central aperture 6 that forms a channel that can be used for catheter placement or for an additional needle.

Figure 4:
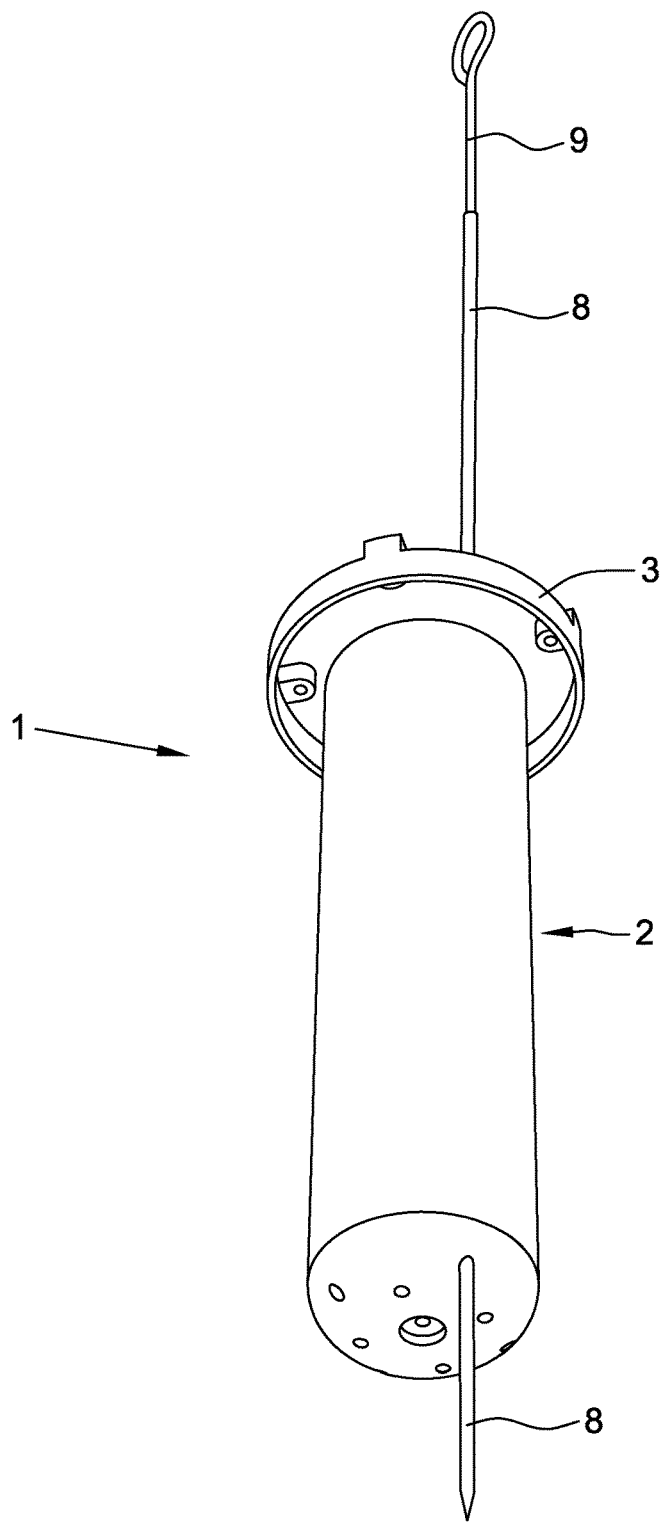
FIG. 4 is a photograph of the apparatus in FIG. 3 showing the needle and metal rod inserted through a channel of the apparatus and showing the needle tip extending from the end of the vaginal cylinder.

The proximal end of the vaginal cylinder 2 shown in FIG. 2 includes eight (8) apertures 5 arranged in a square pattern surrounding a central aperture 6. The distal template 3 shown in FIG. 3 includes eight (8) apertures 5 arranged in a square pattern surrounding a central aperture 6. FIGS. 3 and 4 show a needle 8 and metal rod 9 passing through an aperture 5 of a fully assembled apparatus 1 to demonstrate that the apertures 5 formed in the vaginal cylinder 2 and the distal template 3 are aligned to form a channel (not visible) through the length of the apparatus 1. The channel functions as a guide for positioning the needle 8 to a tumor site. This allows for the orientation of the needles for delivering the treatment. The square pattern of apertures 5 of the apparatus 1 allows for a dose cloud at the apex of the vagina. In use, needles that are capable of delivering therapy are guided by the medical professional through the apertures 5 in the apparatus 1 to the tumor site at the vaginal apex. Advantageously, a patient can be treated on an outpatient basis. Any number of apertures 5 can be formed in the apparatus 1 to generate the desired dose volume distribution. The dose volume distribution can be determined by one skilled in the art such as, for example, a medical professional.

Suitable needles can be determined by one skilled in the art such as a medical professional. Particularly suitable needles can be, for example, plastic flexi-needles and steel needles.

Suitable materials for forming the vaginal cylinder 2 and the distal template 3 include materials that are biocompatible, materials that can be sterilized, materials that can be imaged and combinations thereof. A particularly suitable material for forming the vaginal cylinder 2 and the distal template 3 can be, for example, poly(methyl methacrylate) (e.g., PLEXIGLAS, ACRYLITE, Lucite and Perspex).

APPARATUS FOR BRACHYTHERAPY TREATMENT OF CANCERS IN THE DISTAL TWO-THIRDS OF THE VAGINA

Figure 5:
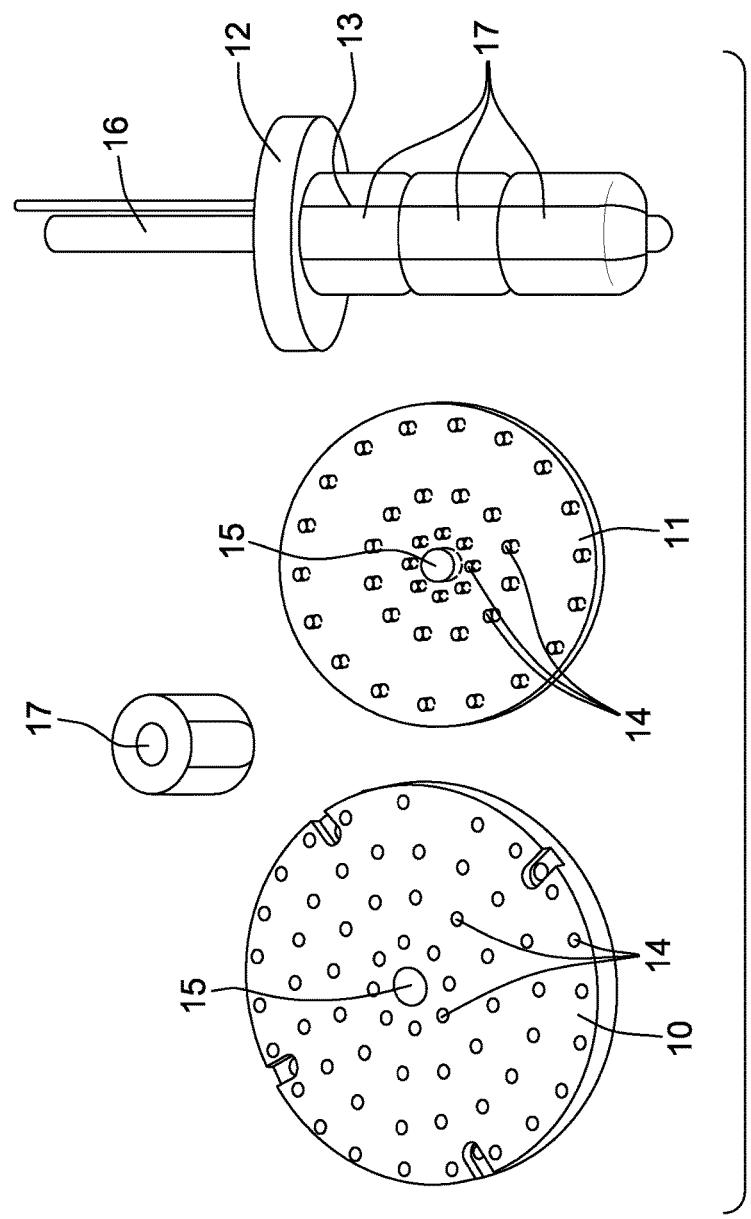
FIG. 5 is a photograph showing two embodiments of distal templates and a third embodiment of the distal template attached to a vaginal cylinder of the present disclosure. The three embodiments of the distal templates are disc-shaped poly(methyl methacrylate) templates having a plurality of apertures for receiving a plurality of needles and a central aperture for receiving a central rod. The central apertures of a distal template and the central aperture of the vaginal cylinder are aligned to form a central channel for receiving the central rod and the inner ring of apertures of the distal template are aligned with a ring of apertures of the vaginal cylinder to form a plurality of channels for receiving a plurality of needles. The embodiment of the vaginal cylinder is an adjustable length applicator for positioning a template that can be lengthened or shortened by adding or removing plastic rings.

In another aspect, the present disclosure is directed to a poly(methyl methacrylate) apparatus including a vaginal cylinder and a distal template that is used for interstitial implantation of HDR brachytherapy needles into cancer tumors in the distal two-thirds of the vagina. FIG. 5 shows two embodiments of distal templates 10, 11 and a third embodiment of the distal template 12 attached to a vaginal cylinder 13 of the present disclosure. The three embodiments of the distal templates 10, 11, 12 are disc-shaped poly(methyl methacrylate) templates having a plurality of apertures 14 arranged in a circular pattern for receiving a plurality of needles that surround a central aperture 15 for receiving a central rod 16. The diameter of the poly(methyl methacrylate) template is selected based on the needed arrangement of needles to generate the optimal dose volume distribution as determined by one skilled in the art such as, for example a medical professional. The diameter of the poly(methyl methacrylate) template 10, 11, 12 can be any desired diameter such that it fits a patient and includes the desired number of apertures 14 to deliver the optimal dose volume distribution. The central aperture 15 of the distal template 10, 11, 12 and the central aperture 15 of the vaginal cylinder 13 are aligned to form a central channel for receiving the central rod 16. The inner ring of apertures surrounding the central aperture 15 of the distal template are aligned with a ring of apertures surrounding the central aperture 15 of the vaginal cylinder 13 to form a plurality of channels for receiving a plurality of needles. The vaginal cylinder 13 shown in FIG. 5 is an adjustable length embodiment that can be lengthened or shortened by adding or removing plastic rings 17.

In use, the vaginal cylinder 13 is inserted into the bodily canal such that the proximal end of the vaginal cylinder 13 is adjacent the tumor. The plurality of needles are inserted through the apertures of the inner rig apertures of the distal template 10, 11, 12 and the vaginal cylinder 13 such that the needle tips are adjacent the tumor. The channels formed by aligning the apertures of the inner rig apertures of the distal template 10, 11, 12 and the vaginal cylinder 13 serve as needle guides through the vaginal cylinder 13 portion of the apparatus. A plurality of needles is also inserted through the apertures of the distal template 10, 11, 12. These needles are pass outside the vaginal cylinder 13 and are positioned adjacent the tumor by a medical professional. The distal template 10, 11, 12 is then fastened, for example using sutures, to the perineum. The needle placement allows for a crescent-shaped dose distribution. The distal poly(methyl methacrylate) template 15. Because the apparatus is made of poly(methyl methacrylate), the templates can be sterilized for reuse and can be imaged by MR.

Apparatus for Treatment of Cancers that are Offset from the Vaginal Apex

Figure 6:
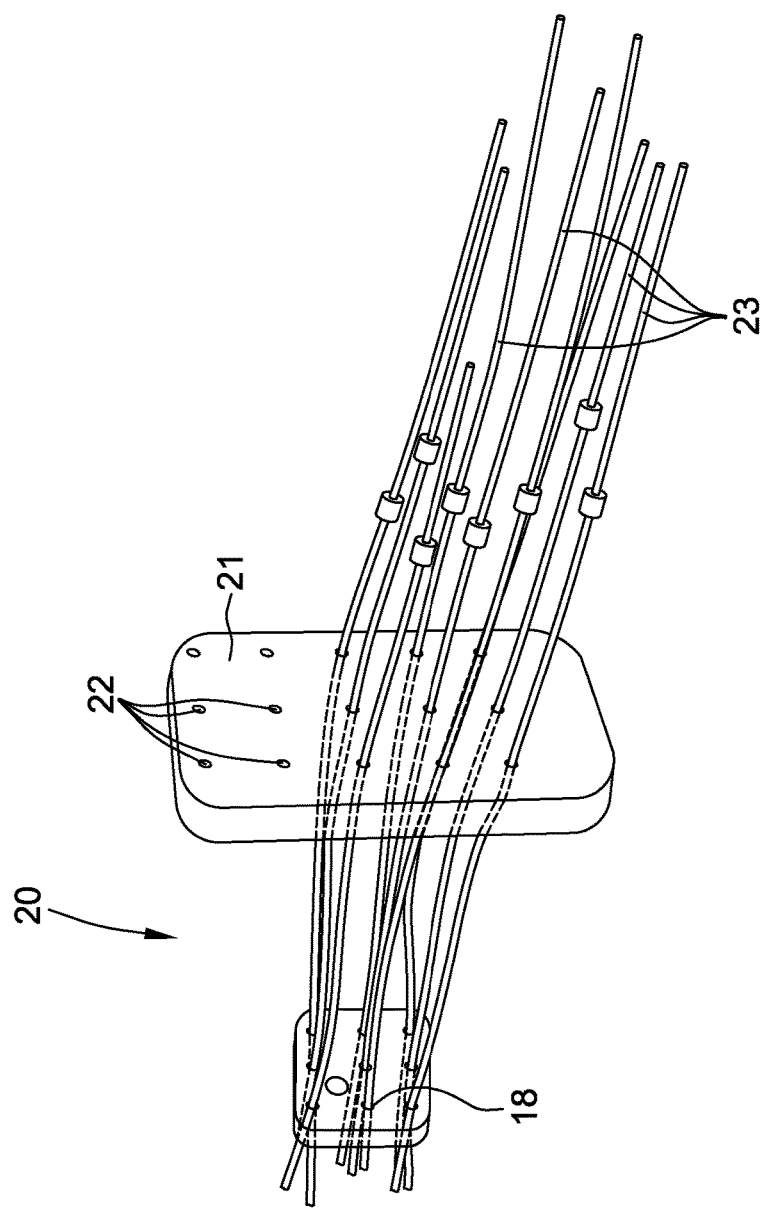
FIG. 6 is a photograph of an apparatus for treatment of cancers that are offset from the vaginal apex showing a poly(methyl methacrylate) proximal template having a plurality of apertures for receiving a plurality of needles and handle for positioning the template at the sides of the vaginal apex.

In another aspect, the present disclosure is directed to a poly(methyl methacrylate) apparatus for treatment of cancers that are offset from the vaginal apex. As shown in FIG. 6, the poly(methyl methacrylate) apparatus includes a proximal poly(methyl methacrylate) template 18. In use, the proximal poly(methyl methacrylate) template 18 is positioned adjacent the tumor using a handle 19. The proximal poly(methyl methacrylate) template 18 is then fastened to the vaginal apex.

Figure 7:
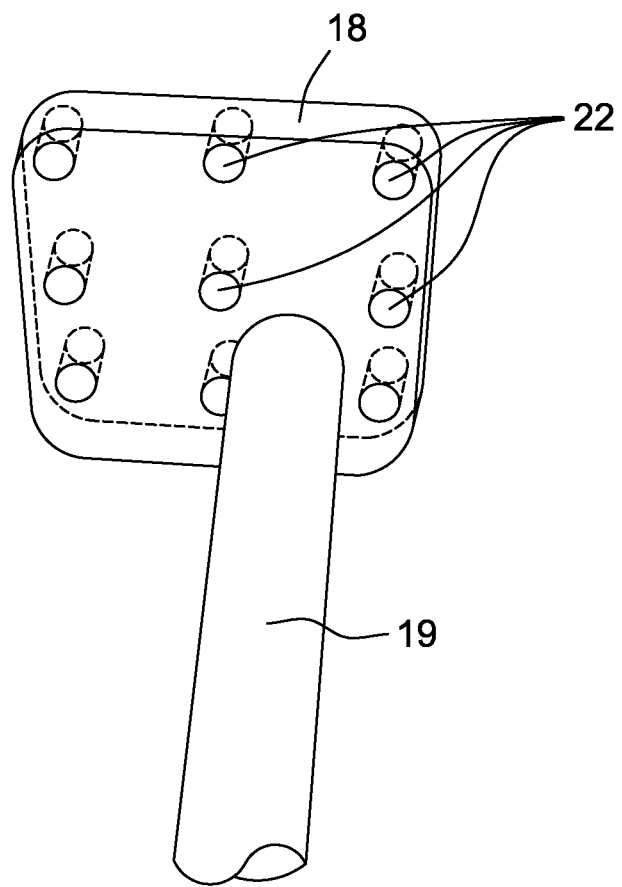
FIG. 7 is a photograph of an apparatus for treatment of cancers that are offset from the vaginal apex showing the poly(methyl methacrylate) proximal template having a plurality of apertures for receiving a plurality of needles of FIG. 6 without the handle and a poly(methyl methacrylate) distal template having a plurality of apertures for receiving a plurality of needles. A plurality of needles is inserted through the proximal template and the distal template to show the apparatus as would be assembled for treatment.

As shown in FIG. 7, the poly(methyl methacrylate) apparatus 20 also includes a distal poly(methyl methacrylate) template 21. As shown in FIGS. 6 and 7, the proximal poly(methyl methacrylate) template 18 and distal poly(methyl methacrylate) template 21 include a plurality of apertures 22. As shown in FIG. 7, a plurality of needles 23 are inserted through the apertures 22 of the proximal poly(methyl methacrylate) template 18 and distal poly(methyl methacrylate) template 21.

In use, the proximal poly(methyl methacrylate) template 18 of the poly(methyl methacrylate) apparatus 20 is placed adjacent the tumor that is offset from the vaginal apex using the handle 19 and fastened such as for example, using sutures. A medical professional then guides needles 23 through the apertures 22 in the proximal poly(methyl methacrylate) template 18. The ends of the needles 23 exit the vaginal cavity and are guided by the medical professional through the apertures 22 in the distal poly(methyl methacrylate) template 21. The distal poly(methyl methacrylate) template 21 is then fastened, for example using sutures, to the perineum. Because the proximal poly(methyl methacrylate) template 18 and the distal poly(methyl methacrylate) template 21 are made of poly(methyl methacrylate), the templates can be sterilized for reuse and can be imaged by MR.

Methods for Guiding the Placement of Brachytherapy Needles

In another aspect, the present disclosure is directed to methods for guiding a plurality of needles to a tumor.

In one aspect, the present disclosure is directed to a method for guiding a plurality of needles to a tumor at the vaginal apex. The method includes: a) positioning adjacent to the tumor a proximal end of a vaginal cylinder of an apparatus, wherein the apparatus comprises: i) a vaginal cylinder comprising a plurality of apertures arranged in a square pattern for receiving a plurality of needles and a central aperture for receiving a central rod; and ii) a distal template comprising a plurality of apertures arranged in a square pattern for receiving a plurality of needles and a central aperture for receiving the central rod; wherein the plurality of apertures in the vaginal cylinder and the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template; b) fastening the apparatus in place; and c) inserting the plurality of needles through the plurality of apertures of the apparatus such that the plurality of needles extend through the plurality of apertures of the vaginal cylinder to a position adjacent to the tumor. In this aspect, all of the needles pass through the apparatus (i.e., the distal template and vaginal cylinder) such that the needle tips extend through the end of the vaginal cylinder to deliver therapy to the tumor site. In this embodiment, the square pattern of apertures in the apparatus allows for a dose cloud to be delivered to the tumor site.

In another aspect, the present disclosure is directed to a method for guiding a plurality of needles to tumor in the distal two-thirds of the vagina. The method includes: a) positioning adjacent to the tumor a proximal end of a vaginal cylinder of an apparatus, wherein the apparatus comprises: i) a vaginal cylinder comprising a plurality of apertures arranged in a circular pattern for receiving a plurality of needles and a central aperture for receiving a central rod; and ii) a distal template comprising a plurality of apertures arranged in a circular pattern for receiving a plurality of needles and a central aperture for receiving the central rod; wherein the plurality of apertures in the vaginal cylinder and an inner ring of the plurality of needles of the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template; b) fastening the apparatus in place; and c) inserting the plurality of needles through the plurality of apertures of the apparatus such that the plurality of needles extend through the channels of the vaginal cylinder to a position adjacent to the tumor; and d) inserting a second plurality of needles through the plurality of apertures of the distal template wherein the second plurality of needles are positioned outside the vaginal cylinder. In this aspect, only the needles inserted in the inner ring of apertures that surround the central aperture pass through the apparatus such that the needle tips extend through the end of the vaginal cylinder to deliver therapy to the tumor site. If an additional needle is inserted through the central rod, it too will pass through the apparatus. Needles that are only inserted through the apertures of the distal template and not through the vaginal cylinder will pass outside the vaginal cylinder. In this method, the medical professional can place the needle tips at the tumor site using the outside of the cylinder as a guide and then place the ends of the needles through apertures of the distal template. In this embodiment, the circular pattern of apertures in the apparatus allows for a crescent-shaped dose distribution to be delivered to the tumor site.

In another aspect, the present disclosure is directed to a method for guiding a plurality of needles for treatment of cancers that are offset from the vaginal apex. The method includes a) positioning a proximal poly(methyl methacrylate) template of a poly(methyl methacrylate) apparatus adjacent the tumor that is offset from the vaginal apex using a handle; b) fastening the proximal poly(methyl methacrylate) template in place; and c) inserting a plurality of needles through the plurality of apertures of the proximal poly (methyl methacrylate) template such that the plurality of needles extend through the apertures of the proximal poly (methyl methacrylate) template to a position adjacent to the tumor; d) inserting the plurality of needles through the apertures of the distal poly(methyl methacrylate) template; and e) fastening the distal poly(methyl methacrylate) template in place. In this method, the medical professional uses the proximal poly(methyl methacrylate) template to place the needle tips at the tumor site. The needle ends then extend through the vaginal cavity to exit the body of the patient. The medical professional then inserts the needle ends through the apertures of the distal template, which is then fastened in place. In this method, a therapy can be delivered to a tumor site that is offset from the vaginal apex. Particularly suitable needles for use in the method are plastic flexi-needles.

The disclosure will be more fully understood upon consideration of the following non-limiting Examples.

EXAMPLES

Example 1

Methods

Forty three patients were treated with twice-daily outpatient-based HDR ISI brachytherapy using Ir-192. Thirty patients (70%) had vaginal lesions, 9 (21%) had vulvar lesions, 2 (5%) urethral, and 2 (5%) cervical. Histologies included 23 squamous cell carcinomas (53%), 13 adenocarcinomas (30%), 2 poorly differentiated carcinomas (5%), and one renal cell carcinoma, one sarcoma, one melanoma, one UPSC, and one polypoid malignant carcinoma. Thirty seven patients (86%) were treated with definitive intent. Three patients (7%) received treatment adjuvantly after surgical resection, and three patients (7%) received palliative local treatment. Thirty-four (79%) received external beam radiation prior to ISI, with a median dose of 50.4 Gy in 1.8 Gy fractions delivered to the primary lesion +/− local-regional lymph nodes. Sixteen patients (37%) received concurrent platinum-based chemotherapy. The apparatus used for delivering therapy included a plastic proximal template attached to an applicator that was inserted through the vaginal canal and sutured to the patient's skin. A foley catheter was in place throughout the duration of treatment. The catheters were cleaned with antiseptic and wrapped in gauze, and the patients wore adult diapers between treatments. A ring-shaped commode cushion was given to each patient for bowel movements. All patients underwent CT simulation for treatment planning purposes. The catheters were loaded using a modified Paris System technique, and dose was prescribed to the isodose surface closest to the implant that encompassed the entire implant volume. Prescribed dose, V100, V150, and V200 were recorded. Patients were followed for local control and toxicities with serial clinical exams and imaging studies, and biopsies were performed when clinically indicated.

Results

Median follow-up from the time of the last delivered treatment was 12 months. Four patients (9%) were admitted to the hospital during treatment—one for pain control, one for nausea control, one for blood transfusion, and one for observation following a fall. Three patients (7%) were seen in the emergency room during treatment and subsequently discharged—one for Foley obstruction, one for a vasovagal episode, and one for an asthma exacerbation. There was no incidence of acute infection in the peri-procedural period. There were 5 significant toxicities (12%) at a median time of 11 months following treatment—three patients developed vaginal/vulvar ulcerations, one developed vaginal radiation necrosis, and one a vaginal abscess. One of the ulcerations occurred following a biopsy. Median prescribed dose was 18 Gy in 2.25 Gy twice-daily fractions. A total of eleven patients (26%) failed locally, and 10 of 37 patients (27%) failed locally that were treated with definitive intent. In patients that were treated definitively, there was no difference in prescribed total dose between patients that failed and those that did not fail locally (BED, $\alpha/\beta=10$: 82 Gy vs. 81 Gy, p=0.625). Patients that failed locally had lower V150N100 and V200/V100 ratios, but this was not statistically significant (0.20 vs. 0.32, p=0.371; 0.059 vs. 0.082, p=0.389).

These results demonstrated that HDR ISI brachytherapy using the apparatus and methods of the present disclosure was feasible, safe, and effective in the treatment of gynecologic malignancies in the outpatient setting. Larger V150N100 and V200/V100 parameters may be associated with improved local control.

What is claimed is:

1. An apparatus for brachytherapy treatment of a patient comprising:
   a vaginal cylinder comprising a proximal end thereon, the proximal end consisting of apertures arranged in a square pattern for receiving a plurality of needles and a central aperture for receiving a central rod, the proximal end defining the apertures being open to exterior the vaginal cylinder such that the plurality of needles can pass beyond the vaginal cylinder through the apertures to facilitate interstitial treatment of tumor tissue; and
   a distal template comprising a suture bracket, the suture bracket comprising an opening for suturing the apparatus to the patient, the distal template further comprising a plurality of apertures arranged in a square pattern for receiving the plurality of needles and a central aperture for receiving the central rod;
   wherein the apertures in the vaginal cylinder and the plurality of apertures in the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template.

2. The apparatus of claim 1, wherein the vaginal cylinder and the distal template are releasably associated.

3. The apparatus of claim 1, wherein the apparatus is image-compatible.

4. The apparatus of claim 1, wherein the vaginal cylinder has a fixed length.

5. The apparatus of claim 1, wherein the vaginal cylinder comprises a plurality of rings, each ring of the plurality of rings including a connection for selectively attaching one of the rings of the plurality of rings to an adjacent ring such that the vaginal cylinder has an adjustable length.

6. The apparatus of claim 1, wherein the apparatus is biocompatible.

7. The apparatus of claim 1, wherein the apparatus is at least one of sterilizable and imagable.

8. The apparatus of claim 1, wherein the apparatus is prepared from poly(methyl methacrylate).

9. A method for guiding a plurality of needles to a tumor for brachytherapy treatment at a vaginal apex of a patient, the method comprising:
   a) positioning adjacent to the tumor a proximal end of a vaginal cylinder of an apparatus, wherein the apparatus comprises:
      i) the vaginal cylinder consisting of apertures on the proximal end arranged in a square pattern for receiving a plurality of needles and a central aperture for receiving a central rod; and
      ii) a distal template comprising a plurality of apertures arranged in a square pattern for receiving the plurality of needles and a central aperture for receiving the central rod;
   wherein the apertures in the vaginal cylinder and the plurality of apertures in the distal template are aligned to form channels for receiving the plurality of needles and wherein the central aperture of the vaginal cylinder and the central aperture of the distal template are aligned to form a central channel for receiving the central rod, wherein the central rod connects the vaginal cylinder and distal template;
   b) fastening the distal template of the apparatus to a tissue of a patient; and
   c) inserting the plurality of needles through the plurality of apertures of the apparatus such that the plurality of needles extend through the apertures of the vaginal cylinder and into the patient to a position adjacent to the tumor.

10. The method of claim 9, wherein the tips of the plurality of needles are positioned at least one of within the tumor and surrounding the tumor.

11. The method of claim 9 wherein the apparatus further comprises a plurality of needles.

12. The method of claim 11, wherein the plurality of needles are selected from the group consisting of plastic needles and steel needles.

* * * * *